(12) United States Patent
Grundler et al.

(10) Patent No.: US 6,953,853 B2
(45) Date of Patent: Oct. 11, 2005

(54) PHTHALAZINONE-PIPERIDINO-DERIVATIVES AS PDE4 INHIBITORS

(75) Inventors: Gerhard Grundler, Constance (DE); Beate Schmidt, Allensbach (DE); Geert Jan Sterk, JJ Utecht (NL)

(73) Assignee: Altana Pharma AG, Constance (DE)

( * ) Notice: Subject to any disclaimer, the term of this patent is extended or adjusted under 35 U.S.C. 154(b) by 222 days.

(21) Appl. No.: 10/467,832

(22) PCT Filed: Feb. 14, 2002

(86) PCT No.: PCT/EP02/01547

§ 371 (c)(1),
(2), (4) Date: Aug. 13, 2003

(87) PCT Pub. No.: WO02/064584

PCT Pub. Date: Aug. 22, 2002

(65) Prior Publication Data

US 2004/0067946 A1 Apr. 8, 2004

(30) Foreign Application Priority Data

Feb. 15, 2001 (EP) .............................................. 01103496

(51) Int. Cl.[7] ............................................ C07D 237/30
(52) U.S. Cl. ..................................................... 544/237
(58) Field of Search .......................... 544/237; 514/248

(56) References Cited

FOREIGN PATENT DOCUMENTS

| | | |
|---|---|---|
| EP | 0 763 534 | 3/1997 |
| EP | 0 934 933 | 8/1999 |
| WO | WO 93/07146 | 4/1993 |
| WO | WO 94/12461 | 6/1994 |
| WO | WO 98/31674 | 7/1998 |
| WO | WO 99/31071 | 6/1999 |
| WO | WO 99/31090 | 6/1999 |
| WO | WO 99/47505 | 9/1999 |
| WO | WO 01/19818 | 3/2001 |
| WO | WO 01/30766 | 5/2001 |
| WO | WO 01/30777 | 5/2001 |
| WO | WO 01/94319 | 12/2001 |

OTHER PUBLICATIONS

Van der Mey, M., et al., "Novel Selective Phosphodiesterase (PDE4) Inhibitors. 4. Resolution, Absolute Configuration, and PDE4 Inhibitory Activity of cis–Tetra– and cis–Hexahydrophthalazinones". J. Med. Chem., 45, 2526–2533, 2002.

Van der Mey, M., et al., "Novel Selective PDE4 Inhibitors. 2. Synthesis and Structure–Activity Relationships of 4–Aryl–Substituted cis–Tetra– and cis–Hexahydrophthalazinones". J. Med. Chem., 44, 2523–2535, 2001.

Norman, Peter, "PDE4 inhibitors 2001. Patent and literature activity 2000–Sep. 2001". Expert Opinion on Therapeutic Patents, 1, 93–111, 2002.

Van der Mey, M., et al., "Novel Selective PDE4 Inhibitors. 1. Synthesis, Structure–Activity Relationships, and Molecular Modeling of 4–(3, 4–Dimethoxyphenyl)–2H–phthalazin–1–ones and Analogues". J. Med. Chem., 2001, 44, 2511–2522.

Van der Mey, M., et al., "Novel Selective PDE4 Inhibitors. 3. In Vivo Anti–inflammatory Activity of a New Series of N–Substituted cis–Tetra– and cis–Hexahydrophthalazinones". J. Med. Chem., 2002, 45, 2520–2525.

*Primary Examiner*—James O. Wilson
*Assistant Examiner*—Zachary C. Tucker
(74) *Attorney, Agent, or Firm*—Nath & Associates PLLC; Joshua B. Goldberg; Sheldon M. McGee

(57) ABSTRACT

The compounds of a formula I, in which the given substituents have the meanings as given in the description, are novel effective PDE4 inhibitors

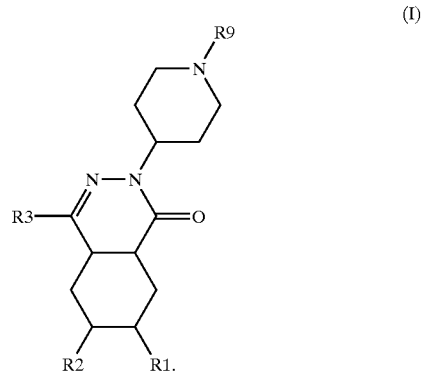

(I)

29 Claims, No Drawings

PHTHALAZINONE-PIPERIDINO-DERIVATIVES AS PDE4 INHIBITORS

FIELD OF APPLICATION OF THE INVENTION

The invention relates to novel piperidino-derivatives, which are used in the pharmaceutical industry for the production of medicaments.

KNOWN TECHNICAL BACKGROUND

International Patent Applications WO98/31674 (=U.S. Pat. No. 6,103,718), WO99/31071, WO99/31090 and WO99/47505 (=U.S. Pat. No. 6,255,303) disclose phthalazinone derivatives having selective PDE4 inhibitory properties. In the International Patent Application WO94/12461 and in the European Patent Application EP 0 763 534 3-aryl-pyridazin-6-one and arylalkyl-diazinone derivatives are described as selective PDE4 inhibitors. International Patent Application WO93/07146 (=U.S. Pat. No. 5,716,954) discloses benzo and pyrido pyridazinone and pyridazinthione compounds with PDEIV inhibiting activity.

DESCRIPTION OF THE INVENTION

It has now been found that the piperidino-derivatives, which are described in greater details below, have surprising and particularly advantageous properties.

The invention thus relates to compounds of formula I

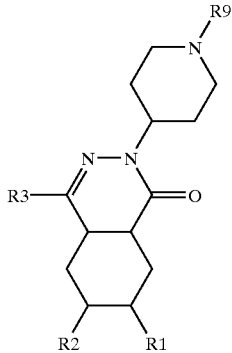

(I)

in which

R1 and R2 are both hydrogen or together form an additional bond,
R3 represents a benzene derivative of formula (a) or (b)

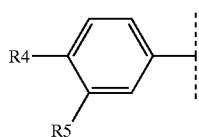

(a)

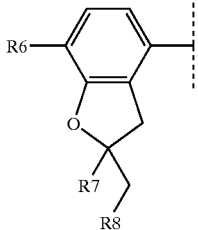

(b)

wherein
R4 is 1–4C-alkoxy or 1–4C-alkoxy which is completely or predominantly substituted by fluorine,
R5 is 1–8C-alkoxy, 3–7C-cycloalkoxy, 3–7C-cycloalkylmethoxy, or 1–4C-alkoxy which is completely or predominantly substituted by fluorine,
R6 is 1–4C-alkoxy, 3–5C-cycloalkoxy, 3–5C-cycloalkylmethoxy, or 1–4C-alkoxy which is completely or predominantly substituted by fluorine,
R7 is 1–4C-alkyl and
R8 is hydrogen or 1–4C-alkyl,
or wherein
R7 and R8 together and with inclusion of the two carbon atoms, to which they are bonded, form a spiro-linked 5-, 6- or 7-membered hydrocarbon ring, optionally interrupted by an oxygen or sulphur atom,
R9 is 1–4C-alkyl, —S(O)$_2$—R10, —S(O)$_2$—(CH$_2$)$_n$—R11, —(CH$_2$)$_m$S(O)$_2$—R12, —C(O)R13, —C(O)—(CH$_2$)$_n$—R14, —(CH$_2$)$_m$—C(O)—R15, Hetaryl, Aryl1 or 1–4C-alkyl-Aryl2,
R10 is 1–4C-alkyl, 5-dimethylaminonaphthalin-1-yl, —N(R16)R17, phenyl or phenyl substituted by R18 and/or R19,
R11 is —N(R16)R17,
R12 is —N(R16)R17,
R13 is 1–4C-alkyl, hydroxycarbonyl-1–4C-alkyl, phenyl, pyridyl, 4-ethyl-piperazin-2,3-dion-1-yl or —N(R16)R17,
R14 is —N(R16)R17,
R15 is —N(R16)R17, phenyl, phenyl substituted by R18 and/or R19 and/or R20,
R16 and R17 are independent from each other hydrogen, 1–7C-alkyl, 3–7C-cycloalkyl, 3–7C-cycloalkylmethyl, phenyl or phenyl substituted by R18 and/or R19 and/or R20, or R16 and R17 together and with inclusion of the nitrogen atom to which they are bonded, form a 4-morpholinyl-, 1-pyrrolidinyl-, 1-piperidinyl-, 1-hexahydroazepino- or a 1-piperazinyl-ring of formula (c)

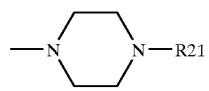

(c)

wherein
R21 is pyrid-4-yl, pyrid-4-ylmethyl, 1–4C-alkyl-dimethylamino, dimethylaminocarbonylmethyl, N-methyl-piperidin-4-yl, 4-morpholino-ethyl or tetrahydrofuran-2-ylmethyl,
R18 is halogen, nitro, cyano, carboxyl, 1–4C-alkyl, trifluoromethyl, 1–4C-alkoxy, 1–4C-alkoxycarbonyl, amino, mono-or di-1–4C-alkylamino, aminocarbonyl 1–4C-alkylcarbonylamino or mono-or di-1–4C-alkylaminocarbonyl, R19 is halogen, amino, nitro, 1–4C-alkyl or 1–4C-alkoxy, R20 is halogen, Hetaryl is pyrimidin-2-yl, thieno-[2,3-d]pyrimidin-4-yl, 1-methyl-1H-pyrazolo-[3,4-d]pyrimidin-4-yl, thiazolyl, imidazolyl or furanyl, Aryl1 is pyridyl, phenyl or phenyl substituted by R18 and/or R19, Aryl2 is pyridyl, phenyl, phenyl substituted by R18 and/or R19, 2-oxo-2H-chromen-7-yl or 4-(1,2,3-thiadiazol-4-yl) phenyl, n is an integer from 1 to 4, m is an integer from 1 to 4, and the salts of these compounds.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, iso-propoxy, ethoxy and methoxy radicals.

1–8C-Alkoxy is a radical which, in addition to the oxygen atom, contains a straight-chain or branched alkyl radical having 1 to 8 carbon atoms. Alkoxy radicals having 1 to 8 carbon atoms which may be mentioned in this context are, for example, the octyloxy, heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy, isopropoxy, ethoxy and methoxy radicals.

Halogen within the meaning of the present invention is bromine, chlorine or fluorine.

3–7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are preferred.

3–7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

3–5C-Cycloalkoxy stands for cyclopropyloxy, cyclobutyloxy and cyclopentyloxy.

3–5C-Cycloalkylmethoxy stands for cyclopropylmethoxy, cyclobutylmethoxy and cyclopentylmethoxy.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1–4C-alkoxy group are replaced by fluorine atoms.

As spiro-linked 5-, 6- or 7-membered hydrocarbon rings, optionally interrupted by an oxygen or sulphur atom, may be mentioned the cyclopentane, cyclohexane, cycloheptane, tetrahydrofuran, tetrahydropyran and the tetrahydrothiophen ring.

1–4C-Alkylcarbonyl is a carbonyl group to which one of the abovementioned 1–4C-alkyl radicals is bonded. An example is the acetyl radical [CH$_3$C(O)—].

An 1–4C-Alkylcarbonylamino radical is, for example, the propionylamino [C$_3$H$_7$C(O)NH—] and the acetylamino radical [CH$_3$C(O)NH—].

Mono- or Di-1–4C-alkylamino radicals contain in addition to the nitrogen atom, one or two of the abovementioned 1–4C-alkyl radicals. Preferred are the di-1–4C-alkylamino radicals, especially the dimethylamino, the diethylamino and the diisopropylamino radical.

Mono- or Di-1–4C-alkylaminocarbonyl radicals contain in addition to the carbonyl group one of the abovementioned mono- or di-1–4C-alkylamino radicals. Examples which may be mentioned are the N-methyl- the N,N-dimethyl-, the N-ethyl-, the N-propyl-, the N,N-diethyl- and the N-isopropylaminocarbonyl radical.

Suitable salts for compounds of the formula I are all acid addition salts. Particular mention may be made of the pharmacologically tolerable inorganic and organic acids customarily used in pharmacy. Those suitable are water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compound of formula I to be emphasized are those in which

R1 and R2 are both hydrogen or together form an additional bond,

R3 represents a benzene derivative of formula (a) or (b)

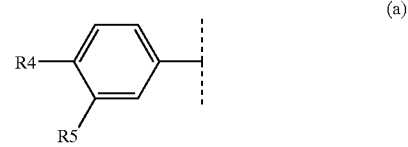

(a)

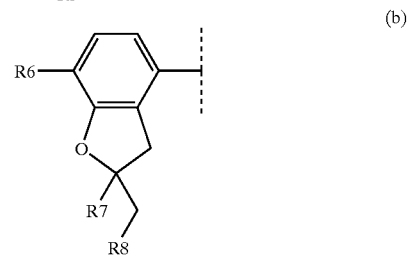

(b)

wherein

R4 is 1–4C-alkoxy or 1–2C-alkoxy which is completely or predominantly substituted by fluorine, R5 is 1–4C-alkoxy,
R6 is 1–2C-alkoxy or 1–2C-alkoxy which is completely or predominantly substituted by fluorine,
R7 is methyl and
R8 is hydrogen,
or wherein
R7 and R8 together and with inclusion of the two carbon atoms, to which they are bonded, form a spiro-linked cyclopentane, cyclohexane, tetrahydrofurane or tetrahydropyran ring,
R9 is 1–4C-alkyl, —S(O)$_2$—R10, —S(O)$_2$—(CH$_2$)$_n$—R11, —C(O)R13, —C(O)—(CH$_2$)$_n$—R14, —(CH$_2$)$_m$—C(O)—R15, Hetaryl, Aryl1 or 1–2C-alkyl-Aryl2,
R10 is 1–4C-alkyl, 5-dimethylaminonaphthalin-1-yl, —N(R16)R17, phenyl or phenyl substituted by R18,
R11 is —N(R16)R17,
R13 is 1–4C-alkyl, hydroxycarbonyl-1–4C-alkyl, phenyl, pyridyl, 4-ethyl-piperazin-2,3-dion-1-yl or —N(R16)R17,
R14 is —N(R16)R17,
R15 is —N(R16)R17, phenyl, phenyl substituted by R18 and/or R19 and/or R20,
R16 and R17 are independent from each other hydrogen, 1–4C-alkyl, phenyl or phenyl substituted by R18 and/or R19 and/or R20, or R16 and R17 together and with inclusion of the nitrogen atom to which they are bonded, form a 4-morpholinyl ring, a 1-piperidinyl ring or a 1-piperazinyl ring of formula (c)

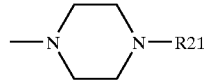

(c)

wherein
R21 is pyrid-4-yl, pyrid-4-ylmethyl, dimethylamino-1–4C-alkyl, dimethylaminocarbonylmethyl, N-methyl-piperidin-4-yl, 4-morpholino-ethyl or tetrahydrofuran-2-ylmethyl,
R18 is halogen, nitro, 1–4C-alkyl, trifluoromethyl, 1–4C-alkoxy or 1–4C-alkoxycarbonyl,
R19 is halogen, amino, nitro, 1–4C-alkyl or 1–4C-alkoxy,
R20 is halogen,
Hetaryl is pyrimidin-2-yl, thieno-[2,3-d]pyrimidin-4-yl or 1-methyl-1H-pyrazolo-[3,4-d]pyrimidin-4-yl,
Aryl1 is pyridyl, phenyl or phenyl substituted by R18,
Aryl2 is pyridyl, phenyl, phenyl substituted by R18, 2-oxo-2H-chromen-7-yl or 4-(1,2,3-thiadiazol-4-yl)phenyl,
n is 1 or 2,
m is 1 or 2,
and the salts of these compounds.

Preferred compounds of formula I are those, in which
R1 and R2 together form an additional bond,
R3 represents a benzene derivative of formula (a) or (b)

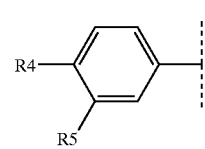

(a)

-continued

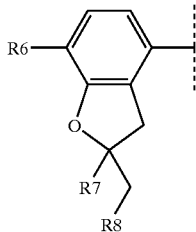

(b)

wherein
R4 is 1–4C-alkoxy,
R5 is 1–4C-alkoxy,
R6 is 1–2C-alkoxy,
R7 is methyl and
R8 is hydrogen,
R9 is 1–4C-alkyl, —S(O)$_2$—R10, —C(O)R13, —C(O)—(CH$_2$)$_n$—R14, —(CH$_2$)$_m$—C(O)—R15, Hetaryl, Aryl1 or 1–2C-alkyl-Aryl2,
R10 is 1–4C-alkyl, 5-dimethylaminonaphthalin-1-yl, phenyl or phenyl substituted by R18,
R13 is 1–4C-alkyl, hydroxycarbonyl-1–4C-alkyl, pyridyl, 4-ethyl-piperazin-2,3-dion-1-yl or —N(R16)R17,
R14 is —N(R16)R17,
R15 is —N(R16)R17, phenyl or phenyl substituted by R18 and/or R19 and/or R20,
R16 and R17 are independent from each other hydrogen, 1–4C-alkyl, phenyl or phenyl substituted by R18 and/or R19 and/or R20, or R16 and R17 together and with inclusion of the nitrogen atom to which they are bonded, form a 4-morpholinyl ring or a 1-piperazinyl ring of formula (c)

(c)

—N⟨   ⟩N—R21 wherein
R21 is dimethylamino-1–4C-alkyl,
R18 is halogen, nitro, 1–4C-alkyl or 1–4C-alkoxycarbonyl,
R19 is amino,
R20 is halogen,
Hetaryl is pyrimidin-2-yl, thieno-[2,3-d]pyrimidin-4-yl or 1-methyl-1H-pyrazolo-[3,4-d]pyrimidin-4-yl,
Aryl1 is phenyl or phenyl substituted by R18,
Aryl2 is pyridyl, phenyl, 2-oxo-2H-chromen-7-yl or 4-(1,2,3-thiadiazol-4-yl)phenyl,
n is 1 or 2,
m is 1 or 2,
and the salts of these compounds.

Particularly preferred compounds of formula I are those in which
R1 and R2 together form an additional bond,
R3 represents a benzene derivative of formula (a) or (b)

(a)

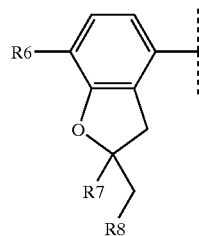

wherein
R4 is methoxy or ethoxy,
R5 is methoxy or ethoxy,
R6 is methoxy or ethoxy,
R7 is methyl and
R8 is hydrogen,
R9 is toluene-4-sulfonyl, methanesulfonyl, acetyl, 5-oxopentanoic acid, pyridin-4-yl-carbonyl, tert-butylaminocarbonyl, phenylaminocarbonyl, 5-dimethylamino-naphthalene-1-sulfonyl, 4-nitrophenyl, pyridin-4-ylmethyl, morpholine-4-carbonyl, 2-(4-amino-3,5-dichlorophenyl-2-oxo-ethyl, 1-methyl-1H-pyrazolo[3,4-d]pyrimidin-4-yl, thieno[2,3-d]pyrimidin-4-yl, pyrimidin-2-yl, 2-oxo-2H-chromen-7-ylmethyl, isopropyl, morpholin-4-yl-2-oxo-ethyl, phenethyl, pyridin-3-ylmethyl, pyridin-2-ylmethyl, pyridin-4-ylmethyl, 2-morpholin-4-ylethanoyl, 2-[4-(2-dimethylamino-ethyl)-piperazin-1-yl]-ethanoyl, isopropylaminocarbonylmethyl, 4-ethyl-piperazine-2,3-dione-1-carbonyl, 4-(1,2,3-thiadiazol-4-yl-)benzyl, 4-ethoxycarbonylphenylamino-2-oxo-ethyl or aminocarbonylmethyl,
and the salts of these compounds.

The compounds of formula I are chiral compounds. Chiral centers exist in the compounds of formula I in the positions 4a and 8a. In case R3 represents a benzene derivative of formula (b) there is one further chiral center in the dihydrofuran-ring, if the substituents —R7 and —CH₂R8 are not identical. However, preferred are in this connection those compounds, in which the substituents —R7 and —CH₂R8 are identical or together and with inclusion of the two carbon atoms to which they are-bonded form a spiro-connected 5-, 6- or 7-membered hydrocarbon ring.

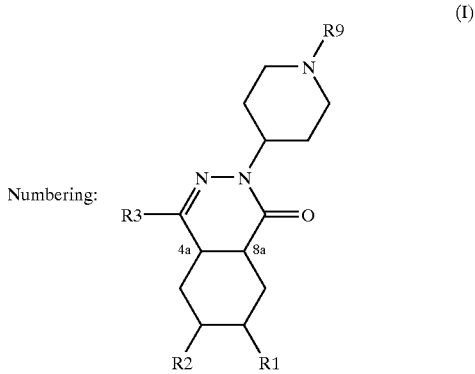

Numbering:

Therefore the invention includes all conceivable pure diastereomers and pure enantiomers of the compounds of formula I, as well as all mixtures thereof independent from the ratio, including the racemates. Preferred are those compounds of formula I, in which the hydrogen atoms in the positions 4a and 8a are cis-configurated. Especially preferred in this connection are those compounds, in which the absolute configuration (according to the rules of Cahn, Ingold and Prelog) is S in the position 4a and R in the position 8a. Racemates can be split up into the corresponding enantiomers by methods known by a person skilled in the art. Preferably the racemic mixtures are separated into two diastereomers during the preparation with the help of an optical active separation agent on the stage of the cyclohexanecarboxylic acids or the 1,2,3,6-tetrahydrobenzoic acids (for example, starting compounds A1, A2 and A3). As separation agents may be mentioned, for example, optical active amines such as the (+)- and (−)-forms of 1-phenylethylamine [(R)-(+)-1-phenylethylamine=(R)-(+)-α-methylbenzylamine or (S)-(−)-1-phenylethylamine=(S)-(−)-α-methylbenzylamine) and ephedrine, the optical active alkaloids quinine, cinchonine, cinchonidine and brucine.

The compounds according to the invention can be prepared, for example, as described in Reaction scheme 1.

Reaction scheme 1:

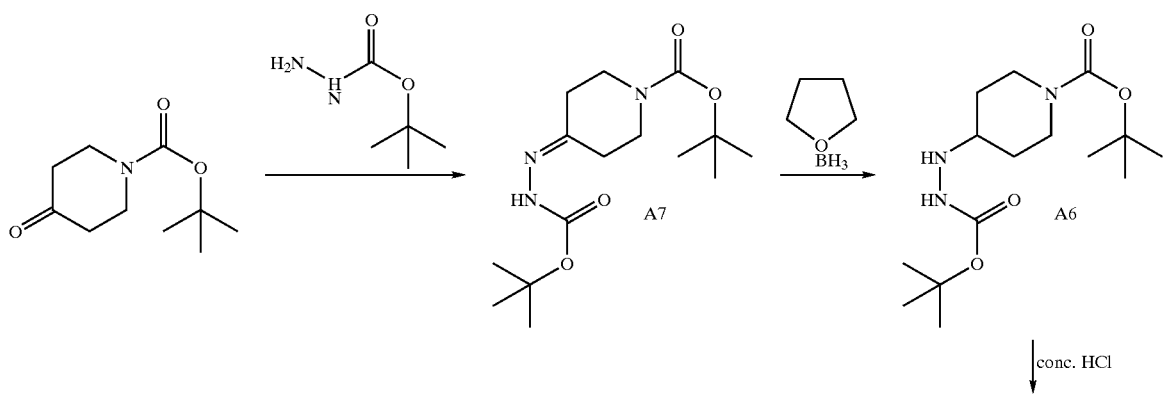

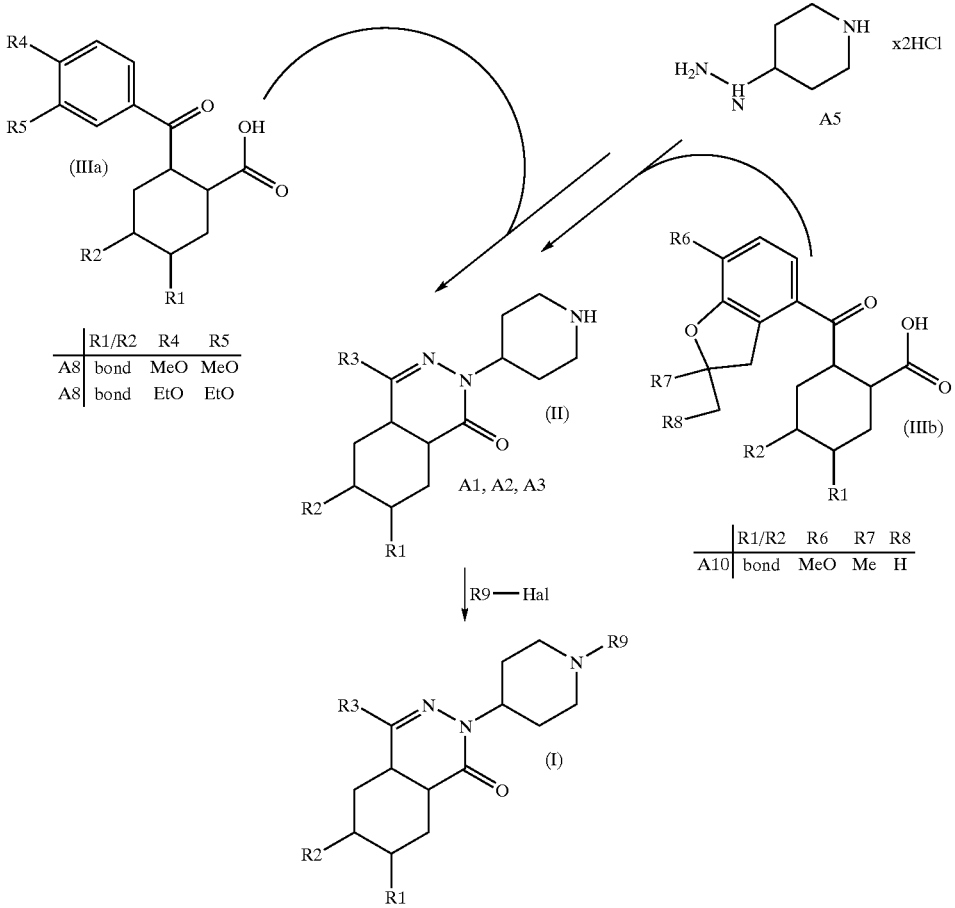

Reaction scheme 1 shows that the compounds of formula I can be, for example, prepared starting from 4-oxo-piperidine-1-carboxylic acid tert-butyl ester which is reacted in a first reaction step with tert-butylcarbazate to give 4-(tert-Butoxycarbonyl-hydrazono)-piperidine-1-carboxylic acid tert-butyl ester (starting compound A7). Compound A7 is reduced with, for example, the boran tetrahydrofurane complex to give 4-(N'-tert-Butoxycarbonyl-hydrazino) piperidine-1-carboxylic acid tert-butyl ester (starting compound A6). Treatment of compound A6 with concentrated hydrochloric acid results in the formation of piperidin-4-yl-hydrazine dihydrochloride (starting compound A5).

The reaction of piperidin-4-yl-hydrazine dihydrochloride with cyclohexanecarboxylic acids or 1,2,3,6-tetrahydrobenzoic acids of formulae IIIa or IIIb leads to the piperidino derivatives of formula II.

These are reacted in the final reaction step with compounds of formula R9-X, wherein X represents a suitable leaving group, preferably a chlorine atom, to give the compounds of formula I.

For some compounds of formula I, it can be advantageous, to introduce the substituent R9 in two reaction steps. As example may be mentioned those compounds of formula I, wherein R9 represents morpholin-4-ylethanoyl. Here, the corresponding compounds of formula II are reacted in a first step with chloroacetylchloride and then in a second step with morpholine.

Suitably, the conversions are carried out analogous to methods which are familiar per se to the person skilled in the art, for example, in the manner which is described in the following examples.

The preparation of the cyclohexanecarboxylic acids and 1,3,5,6-tetrahydrobenzoic acids of the formulae IIIa or IIIb is described, for example, in WO98/31674, WO99/31090 and WO99/47505.

The substances according to the invention are isolated and purified in a manner known per se, e.g. by distilling off the solvent in vacuo and recrystallising the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula I, of which the preparation is explicitly not described, can be prepared in an analogous way or in a way which is known by a person skilled in the art using customary preparation methods.

The compounds, which are mentioned in the examples as well as their salts are preferred compounds of the invention.

EXAMPLES

Final Products

1. (4aS,8aR)-4-(3,4-Diethoxyphenyl)-2-[1-(toluene-4-sulfonyl)-piperidin-4-yl]-4a,5,8,8a-tetrahydro-2H-phthalazin-1-one A solution of 1.0 g of starting compound A2 and 1.0 g of p-toluenesulfonyl chloride in 50 ml of pyridine is stirred at RT for 18 h after which the mixture is evaporated. The residue is partitioned between aqueous sodium carbonate and dichloromethane. The dichloromethane layer is dried over magnesium sulfate and evaporated. The compound is crystallised from methanol. M. p. 99–101° C.

2. (4aS,8aR)-4-(3,4-diethoxyphenyl)-2-(1-methanesulfonyl-piperidin-4-yl)-4a,5,8,8a-tetrahydro-2H-phthalazin-1-one Prepared from methanesulfonylchloride and starting compound A2 as described for compound 1. Crystallisation from methanol/water. M. p. 99–102° C.

3. (4aS,8aR)-2-(1-Acetyl-piperidin-4-yl)-4-3,4-diethoxyphenyl)-4a,5,8,8a-tetrahydro-2H-phthalazin-1-one Prepared from acetic anhydride and starting compound A2 as described for compound 1. Crystallised from diethyl ether. M. p. 148–150° C.

4. 5-(4-[(4aS,8aR)-4-(3,4-Diethoxy-phenyl)-1-oxo-4a,5,8,8a-tetrahydro-1H-phthalazin-2-yl]-piperidin-1-yl)-5-oxo-pentanoic Acid Prepared from glutaric anhydride and starting compound A2 as described for compound 1. After evaporating the pyridine, the residue is partitioned between ethyl acetate and 1N hydrochloric acid. The ethyl acetate solution is dried over magnesium sulfate and evaporated. Crystallisation from diethyl ether. M. p. 133–135° C.

5. (4aS,8aR)4-(3,4-Diethoxyphenyl)-2-[1-(1-pyridin-4-yl-methanoyl)-piperidin-4-yl]-4a,5,8,8a-tetrahydro-2H-phthalazin-1-one Hydrochloride Prepared from isonicotinoyl chloride hydrochloride and starting compound A2 as described for compound 1. After evaporating the dichloromethane solution, the residue is dissolved in diethyl ether. After addition of a saturated solution of hydrochloric acid in ether, the titel compound precipitates. M. p. 66–68° C.

6. 4-[(4aS,8aR)-4-(3,4-Diethoxyphenyl)-1-oxo-4a,5,8,8a-tetrahydro-1H-phthalazin-2-yl]-piperidine-1-carboxylic Acid tert-butylamide A mixture of 1.0 g of starting compound A2, 0.5 g of t-butylisocyanate and 2 ml of triethylamine in 50 ml of tetrahydrofurane is stirred for 18 h at RT. After evaporating the solution, the residue is partitioned between water and ethyl acetate. Crystallisation from a mixture of dichloromethane and petroleum ether (60–80° C.). M. p. 145–148° C.

7. 4-[(4aS,8aR)-4-(3,4-Diethoxyphenyl)-1-oxo-4a,5,8,8a-tetrahydro-1H-phthalazin-2-yl]-piperidine-1-carboxylic Acid Phenylamide Prepared from starting compound A1 and phenylisocyanate as described for compound 6. Crystallisation from ether. M. p. 109–112° C.

8. 4-[(4aS,8aR)-4-(3,4-Dimethoxyphenyl)-1-oxo-4a,5,8,8a-tetrahydro-1H-phthalazin-2-yl]-piperidine-1-carboxylic Acid Tert-butylamide Prepared from starting compound A1 and t-butylisocyanate as described for compound 6. Crystallisation from ether. M. p. 164–166° C.

9. (cis)-4-[4-(7-Methoxy-2,2-dimethyl-2,3-dihydro-benzofuran-4-yl)-1-oxo-4a,5,8,8a-tetrahydro-1H-phthalazin-2-yl]-piperidine-1-carboxylic Acid Tert-butylamide Prepared from starting compound A3 and t-butylisocyanate as described for compound 6. Crystallisation from ether. M. p. 145–147° C.

10. (4aS,8aR)-4-(3,4-Dimethoxyphenyl)-2-[1-(5-dimethylamino-naphthalene-1-sulfonyl)-piperidin-4-yl]-4a,5,8,8a-tetrahydro-2H-phthalazin-1-one Prepared from dansylchloride and starting compound A1 as described for compound 1. Crystallisation from methanol. M. p. 198–200° C.

11. (4aS,8aR)-4-(3,4-Dimethoxyphenyl)-2-[1-(4-nitro-phenyl)-piperidin-4-yl]-4a,5,8,8a-tetrahydro-2H-phthalazin-1-one A mixture of 1.0 g of compound A1, 1.0 g of 1-Iodo-4-nitrobenzene and 1.0 g of potassium carbonate in 20 ml of dimethylformamide is stirred for 18 h at RT after which 100 ml of water is added to the reaction mixture. The precipitate is filtered off and crystallised from methanol. M. p. 196–197° C.

12. (4aS,8aR)-4-(3,4-Dimethoxyphenyl)-2-(1-pyridin-4-ylmethyl-piperidin-4-yl)-4a,5,8,8a-tetrahydro-2H-phthalazin-1-one Prepared from starting compound A1 and 4-picolylchloride hydrochloride as described for compound 11. After the addition of 100 ml of water, 20 ml of diethyl ether is added and the resulting mixture stirred for 30 min. The precipitate is filtered off and dried. M. p. 196–197° C.

13. (4aS,8aR)-4-(3,4-Dimethoxyphenyl)-2-1-(morpholine-4-carbonyl)-piperidin-4-yl]-4a,5,8,8a-tetrahydro-2H-phthalazin-1-one Prepared from 4-morpholinocarbonyl chloride and compound A1 as described for compound 1. Crystallisation from diethyl ether. M. p. 184–185° C.

14. (4aS,8aR)-2-[1-2-(4-Amino-3,5-dichloro-phenyl)-2-oxo-ethyl]-piperidin-4-yl)-4-(3,4-dimethoxy-phenyl)-4a,5,8,8a-tetrahydro-2H-phthalazin-1-one Hydrochloride Prepared from (4-Amino-3,5dichloro-phenyl)-2-bromo-ethanone and starting compound A1 as described for compound 11. After the addition of water, the mixture is extracted with diethyl ether. The ether solution is dried over magnesium sulfate. After the addition of a saturated solution of hydrochloric acid in ether, the compound precipitates. Crystallisation from tetrahydrofurane. M. p. 206° C. (decomposition).

15. 4-(3,4-Dimethoxyphenyl)-2-[1-(1-methyl-1H-pyrazolo[3,4-d]pyrimidin-4-yl)-piperidin-4-yl]4a,5,8,8a-tetrahydro-2H-naphthalen-1-one Prepared from 4-Chloro-7-methyl-7H-pyrrolo[2,3-d]pyrimidine and starting compound A1 as described for compound 11. Crystallisation from methanol. M. p. 193–194° C.

16. (4aS,8aR)-4-(3,4-Dimethoxyphenyl)-2-(1-thieno
[2,3-d]pyrimidin-4-yl-piperidin-4-yl)-4a,5,8,8a-
tetrahydro-2H-phthalazin-1-one Prepared from 4-Chloro-thieno[2,3-d]pyrimidine and starting compound A1 as described for compound 11. After the addition of water, the mixture is extracted with diethyl ether. The ether solution is dried over magnesium sulfate. After the addition of a saturated solution of hydrochloric acid in ether, the compound precipitates. M. p. 219–220° C.

17. (4aS,8aR)-4-(3,4-Dimethoxyphenyl)-2-(1-
pyrimidin-2-yl-piperidin-4-yl)-4a,5,8,8a-tetrahydro-
2H-phthalazin-1-one Prepared from 2-Chloro-pyrimidine and starting compound A1 as described for compound 11. Crystallisation from methanol. M. p. 163–166° C.

18. (4aS,8aR)-4-(3,4-Dimethoxyphenyl)-2-[1-(2-
oxo-2H-chromen-7-ylmethyl)-piperidin-4-yl]-4a,5,8,
8a-tetrahydro-2H-phthalazin-1-one Hydrochloride Prepared from 7-Chloromethyl-chromen-2-one and starting compound A1 as described for compound 11. After the addition of water, the mixture is extracted with diethyl ether. The ether solution is dried over magnesium sulfate. After the addition of a saturated solution of hydrochloric acid in ether, the compound precipitates. M. p. 264–267° C.

19. 4-(3,4-Dimethoxyphenyl)-2-(1-Isopropyl-
piperidin-4-yl)-4a,5,8,8a-tetrahydro-2H-phthalazin-
1-one Hydrochloride Prepared from 2-iodopropane and starting compound A1 as described for compound 18. M. p. 158–159° C.

20. (4aS,8aR)-4-(3,4-Dimethoxyphenyl)-2-[1-(2-
morpholin-4-yl-2-x-ethyl)-piperidin-4-yl]-4a,5,8,8a-
tetrahydro-2H-phthalazin-1-one Hydrochloride Prepared from 4-(2-chloroacetyl)morpholine and starting compound A1 as described for compound 18. M. p. 159–162° C.

21. (4aS,8aR)4-(3,4-Dimethoxyphenyl)-2-(1-
phenethyl-piperidin-4-yl)-4a,5,8,8a-tetrahydro-2H-
phthalazin-1-one Hydrochloride Prepared from 2-bromoethylbenzene and starting compound A1 as described for compound 18. M. p. 216–217° C.

22. (4aS,8aR)4-(3,4-Diethoxyphenyl)-2-[1-
(morpholine-4-carbonyl)-piperidin-4-yl]-4a,5,8,8a-
tetrahydro-2H-phthalazin-1-one Prepared from 4-morpholinocarbonyl chloride and starting compound A2 as described for compound 1. Crystallisation from diethyl ether. M. p. 139–141° C.

23. (4aS,8aR)-4-(3,4-Dimethoxyphenyl)-2-(1-
pyridin-3-ylmethyl-piperidin-4-yl)-4a,5,8,8a-
tetrahydro-2H-phthalazin-1-one Dihydrochloride Prepared from starting compound A1 and 3-picolylchloride hydrochloride as described for compound 18. M. p. 252–254° C.

24. (4aS,8aR)-4-(3,4-Dimethoxy-phenyl)-2-(1-
pyridin-2-ylmethyl-piperidin-4-yl)-4a,5,8,8a-
tetrahydro-2H-phthalazin-1-one Dihydrochloride Prepared from compound A1 and 2-picolylchloride hydrochloride as described for compound 18. M. p. 214–216° C.

25. (4aS,8aR)-4-(3,4-Diethoxyphenyl)-2-[1-(2-
morpholin-4-yl-ethanoyl)-piperidin-4-yl]-4a,5,8,8a-
tetrahydro-2H-phthalazin-1-one Hydrochloride Prepared from starting compound A5 and morpholine as described for compound 18. M. p. 219° C. (decomposition).

26. (4aS,8aR)-4-(3,4-Diethoxyphenyl)-2-(1-(2-[4-(2-
dimethylamino-ethyl)-piperazin-1-yl]-ethanoyl)-
piperidin-4-yl)-4a,5,8,8a-tetrahydro-2H-phthalazin-
1-one Trihydrochloride Prepared from starting compound A4 and dimethyl-(2-piperazin-1-yl-ethyl)-amine as described for compound 18. M. p. 195–197° C.

27. 2-(4-[(4aS,8aR)-4-(3,4-Dimethoxyphenyl)-1-
oxo-4a,5,8,8a-tetrahydro-1H-phthalazin-2-yl]-
piperidin-1-yl)-2H-isopropyl-acetamide Prepared from starting compound A1 and N-(chloroacetyl)isopropylamine as described for compound 11. Crystallisation from ether. M. p. 172–173° C.

28. (4aS,8aR)4-(3,4-Dimethoxyphenyl)-2-[1-(4-1,2,
3-thiadiaz 1-4-yl-benzyl)-piperidin-4-yl]-4a,5,8,8a-
tetrahydro-2H-phthalazin-1-one Dihydrochloride Prepared from starting compound A1 and 4-(4-Bromomethyl-phenyl)-[1,2,3]thiadiazole as described for compound 18. M. p. 243–245° C.

29. 1(1-(4-[(4aS,8aR)-4-(3,4-Dimethoxyphenyl)-1-
oxo-4a,5,8,8a-tetrahydro-1H-phthalazin-2-yl]-
piperidin-1-yl)-methanoyl)-4-ethyl-piperazine-2,3-
dione Prepared from 4-ethyl-2,3-dioxo-piperazine-1-carbonyl chloride and starting compound A1 as described for compound 1. Crystallisation from ethyl acetate/diethyl ether. M. p. 226–228° C.

30. 4-(2-(4-[(4aS,8aR)-4-(3,4-Dimethoxy-phenyl)-1-
oxo-4a,5,8,8a-tetrahydro-1H-phthalazin-2-yl]-
piperidin-1-yl)-ethanoylamino)-benzoic Acid Ethyl
Ester Hydrochloride Prepared from ethyl 4-(2-chloroacetamido)benzoate and starting compound A1 as described in example 18. M. p. 153–156° C.

31. 2-(4[(4aS, 8aR)-4-(3,4-Dimethoxyphenyl)-1-
oxo-4a,5,8,8a-tetrahydro-1H-phthalazin-2-yl]-
piperidin-1yl)-2H-acetamide Hydrochloride Prepared from 2-chloroacetamide and starting compound A1 as described for compound 16. M. p. 241–243° C.

Starting Compounds

A1. (4aS,8aR)-4-(3,4-Dimethoxy-phenyl)-2-
piperidin-4-yl-4a,5,8,8a-tetrahydro-2H-phthalazin-1-
one Hydrochloride A solution of 50 mmol of the salt of (S)-(−)-α-methylbenzylamine and (cis)-2-(3,4-dimethoxybenzoyl)-1,2,3,6-tetrahydrobenzoic acid (starting compound A8), 55 mmol of piperidin-4-yl-hydrazine dihydrochloride and 100 mmol of triethylamine in 150 ml of 1-propanol is refluxed for 18 h. After cooling to RT, the precipitate is filtered off and dried. M. p. 285–288° C.

A2. (4aS,8aR)-4-(3,4-Diethoxy-phenyl)-2-piperidin-
4-yl-4a,5,8,8a-tetrahydro-2H-phthalazin-1-one
Hydrochloride Prepared from the salt of (S)-(−)-α-methylbenzylamine and (cis)-2-(3,4-diethoxybenzoyl)-1,2,3,6- tetrahydrobenzoic acid (starting compound A9) in 2-propanol as described for compound A1. M. p. 248–250° C.

A3. (cis)-4-(7-Methoxy-2,2-dimethyl-2,3-dihydro-benzofuran-4-yl)-2-piperidin-4-yl-4a,5,8,8a-tetrahydro-2H-phthalazin-1-one Hydrochloride Prepared from (cis)-2-(2,3-Dihydro-2,2-dimethyl-7-methoxybenzofuran-4 carbonyl)-1,2,3,6-tetrahydrobenzoic acid (starting compound A10) in 1-propanol as described for compound A1. After evaporating the solvent, the residue is partitioned between dichloromethane and aqueous sodium carbonate. The dichlormethane layer is dried over magnesium sulfate and evaporated. The residue is dissolved in dichloromethane and after the addition of a solution of hydrochloric acid in ether, the compound precipitates. M. p. 288–290° C.

A4. (4aS,8aR)-2-[1-(2-Chloro-acetyl)-piperidin-4-yl]4-(3,4-diethoxy-phenyl)-4a,5,8,8a-tetrahydro-2H-phthalazin-1-one A solution of 15 mmol of chloroacetylchloride in 10 ml of dichloromethane is added to a solution of 15 mmol of starting compound A2 and 8 ml of trietylamine in 50 ml of dichloromethane at 0° C. After complete addiotion, the mixture is stirred for another 45 min after which 50 ml of water is added. The dichlormethane solution is dried over magnesium sulfate and evaporated. The residue is purified by chromatography. Elution with a 2/1 mixture of ethyl acetate and petroleum ether (60–80° C.). Crystallisation from hexane. M. p. 135–136° C.

A5. Piperidin-4-yl-hydrazine Dihydrochloride

A mixture of 0.1 mole of 4-(N'-tert-Butoxycarbonyl-hydrazino)-piperidine-1-carboxylic acid tert-butyl ester (starting compound A6) and 150 ml of concentrated hydrochloric acid is heated at 90° C. for 60 min after which the clear solution is evaporated. The residue is washed with tetrahydrofurane, filtered off and dried under vacuum. M. p. 256–259° C.

A6. 4-(N'-tert-Butoxycarbonyl-hydrazino)-piperidine-1-carboxylic acid tert-butyl Ester 150 ml of a solution of borohydride in tertahydrofurane (1.0 mol/l) is slowly added to a solution of 0.12 mole of 4-(tert-Butoxycarbonyl-hydrazono)-piperddine-1-carboxylic acid tert-butyl ester (starting compound A7) in 100 ml of dry tetrahydrofurane. After complete addition, the mixture is stirred for another 30 min after which a 100 ml of water is added to destroy the excess of borohydride. Subsequently the tetrahydrofurane is evaporated and the resulting aqeous solution extracted with diethyl ether. After drying the solvent over magnesium sulfate, the ether is evaporated. M. p. 112–115° C.

A7. 4-(tert-Butoxycarbonyl-hydrazono)-piperidine-1-carboxylic acid tert-butyl Ester A mixture of 0.15 mole of 4-oxo-piperidine-1-carboxylic acid tert-butyl ester (commercially available) and 0.15 mole of tert-butylcarbazate in 250 ml of hexane is stirred for 18 h at RT. The precipitate is filtered off and dried under vacuum. M. p. 172–174° C.

A8. (cis)-2-(3,4-Dimethoxybenzoyl)-1,2,3,6-tetrahydrobenzoic acid

Prepared as described in WO98/31674.

A9. (cis)-2-(3,4-diethoxybenzoyl)-1,2,3,6-tetrahydrobenzoic acid

Prepared as described in WO99/47505.

A10. (cis)-2-(2,3-Dihydro-2,2-dimethyl-7-methoxybenzofuran-4carbonyl)-1,2,3,6-tetrahydrobenzoic Acid Prepared as described in WO99/31090.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which-are based onallergic and/or chronic, immunological false reactions In the region of the upper airways (pharynx, nose) and the adjacent regions (paranasal sinuses, eyes), such as allergic rhinitis/sinusitis, chronic rhinitis/ sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multinfarct dementia; and also Illnesses of the central nervous system, such as depressions or arteriosclerotic dementia.

The invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of medicaments which are employed for the treatment and/or prophylaxis of the illnesses mentioned.

The invention furthermore relates to medicaments for the treatment and/or prophylaxis of the Illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The medicaments are prepared by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar with auxiliaries which are suitable for the desired pharmaceutical formulations on account of his expert knowledge. In addition to solvents, gel formers, ointment bases and other active compound excipients, for example antioxidants, dispersants, emulsifiers, preservatives, solubilizers or permeation promoters, can be used.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pearshaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarly between 0.1 and 3 mg per day. The customary dose in the case of systemic therapy (p.o. or i.v.) is between 0.03 and 3 mg/kg per day.

Biological investigations

The second messenger cyclic AMP (CAMP) is well-known for inhibiting inflammatory and immunocompetent cells. The PDE4 isoenzyme is broadly expressed in cells involved in the initiation and propagation of inflammatory diseases (H Tenor and C Schudt, In "Phosphodiesterase Inhibitors", 21–40, "The Handbook of Immunopharmacology", Academic Press, 1996), and its inhibition leads to an increase of the intracellular CAMP concentration and thus to the inhibition of cellular activation (J E Souness et al., Immunopharmacology 47:127–162, 2000).

The antiinflammatory potential of PDE4 inhibitors in vivo in various animal models has been described (M M Telxeira, TIPS 18: 164–170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682–690, 1991) or eosinophilic (A Hatzelmann et al., Brit J Pharmacol 114: 821–831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221–231, 1997, and Pulmonary Pharmacol Therap 12: 377–386, 1999). In addition, the immunomodulatory potential of PDE4 inhibitors is evident from the inhibition of T-cell responses like cytokine synthesis or proliferation (D M Essayan, Biochem Pharmacol 57: 965–973, 1999). Substances which inhibit the secretion of the afore-mentioned proinflammatory mediators are those which inhibit PDE4. PDE4 inhibition by the compounds according to the invention is thus a central indicator for the suppression of inflammatory processes.

Method for Measuring Inhibition of PDE4 Activity

PDE4 activity was determined as described by Thompson et al. (Adv Cycl Nucl Res 10: 69–92, 1979) with some modifications (Bauer and Schwabe, Naunyn-Schmiedeberg's Arch Pharmacol 311: 193–198, 1980). At a final assay volume of 200 µl (96 well microtiter plates) the assay mixture contained 20 mM Tris (pH 7.4), 5 mM $MgCl_2$, 0.5 µM cAMP, [$^3$H]cAMP (about 30,000 cpm/assay), the test compound and an aliquot of cytosol from human neutrophils which mainly contains PDE4 activity as described by Schudt et al. (Naunyn-Schmiedeberg's Arch Pharmacol 344: 682–690, 1991); the PDE3-specific inhibitor Motapizone(1 µM) was-included to suppress PDE3 activity originating from contaminating platelets. Serial dilutions of the compounds were prepared in DMSO and further diluted 1:100 (v/v) in the assays to obtain the desired final concentrations of the inhibitors at a DMSO concentration of 1% (v/v) which by itself only slightiy affected PDE4 activity.

After preincubation for 5 min at 37° C., the reaction was started by the addition of substrate (cAMP) and the assays were incubated for further 15 min at 37° C. 50 µl of 0.2 N HCl was added to stop the reaction and the assays were left on Ice for about 10 min. Following incubation with 25 µg 5'-nucleotidase (Crotalus atrox snake venom) for 10 min at 37° C., the assays were loaded on QAE Sephadex A-25 (1 ml bed volume). The columns were eluted with 2 ml of 30 mM ammonium formlate (pH 6.0) and the eluate was counted for radioactivity. Results were corrected for blank values (measured in the presence of denatured protein) which were below 5% of total radioactivity. The amount of cyclic nucleotides hydrolyzed did not exceed 30% of the original substrate concentration. The $IC_{50}$-values for the compounds according to the invention for the inhibition of the PDE4 activity were determined from the concentration-inhibition curves by nonlinear-regression.

The inhibitory values determined for the compounds according to the invention follow from the following table A, in which the numbers of the compounds correspond to the numbers of the examples.

TABLE A

Inhibition of PDE4 acitivity [measured as $-logIC_{50}$ (mol/l)]

| compound | $-logIC_{50}$ |
|---|---|
| 7 | 10.28 |
| 8 | 10.18 |
| 9 | 10.65 |

TABLE A-continued

Inhibition of PDE4 acitivity [measured as $-logIC_{50}$ (mol/l)]

| compound | $-logIC_{50}$ |
|---|---|
| 10 | 9.57 |
| 11 | 10.34 |
| 12 | 10.79 |
| 13 | 10.03 |
| 14 | 10.33 |
| 15 | 10.27 |
| 16 | 10.50 |
| 17 | 10.51 |
| 18 | 10.32 |
| 20 | 10.40 |
| 21 | 9.69 |
| 22 | 9.37 |
| 23 | 10.80 |
| 24 | 10.63 |
| 25 | 10.19 |
| 27 | 10.37 |
| 28 | 10.24 |
| 29 | 10.87 |
| 31 | 9.20 |

What is claimed is:
1. A compound of formula I

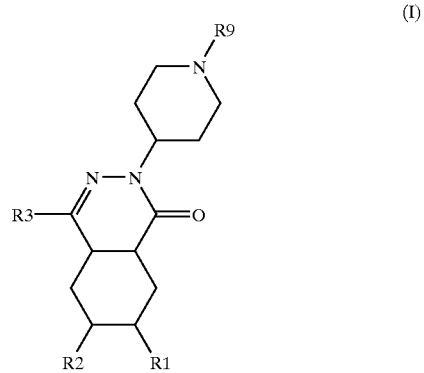

in which
R1 and R2 are both hydrogen or together form an additional bond,
R3 represents a benzene derivative of formula (a) or (b)

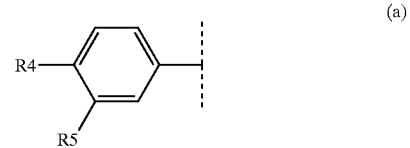

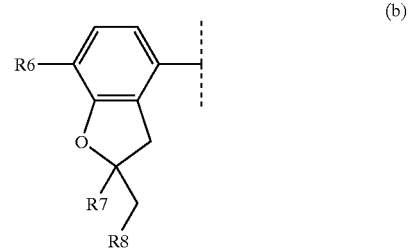

wherein
R4 is 1–4C-alkoxy or 1–4C-alkoxy which is completely or predominantly substituted by fluorine,
R5 is 1–8C-alkoxy, 3–7C-cycloalkoxy, 3–7C-cycloalkylmethoxy, or 1–4C-alkoxy which is completely or predominantly substituted by fluorine,
R6 is 1–4C-alkoxy, 3–5C-cycloalkoxy, 3–5C-cycloalkylmethoxy, or 1–4C-alkoxy which is completely or predominantly substituted by fluorine,
R7 is 1–4C-alkyl and
R8 is hydrogen or 1–4C-alkyl,
or wherein
R7 and R8 together, and with inclusion of the two carbon atoms, to which they are bonded, form a spiro-linked 5-, 6- or 7-membered hydrocarbon ring, optionally interrupted by an oxygen or sulphur atom,
R9 is —S(O)$_2$—R10, —S(O)$_2$—(CH$_2$)$_n$—R11, —(CH$_2$)$_m$—S(O)$_2$—R12, —C(O)R13, —C(O)—(CH$_2$)$_n$—R14, —(CH$_2$)$_m$—C(O)—R15, Hetaryl, Aryl1 or Aryl2-1–4C-alkyl,
R10 is 1–4C-alkyl, 5-dimethylaminonaphthalin-1-yl, —N(R16)R17, phenyl or phenyl substituted by R18 and/or R19,
R11 is —N(R16)R17,
R12 is —N(R16)R17,
R13 is 1–4C-alkyl, hydroxycarbonyl-1–4C-alkyl, phenyl, pyridyl, 4-ethyl-piperazin-2,3-dion-1-yl or —N(R16)R17,
R14 is —N(R16)R17,
R15 is —N(R16)R17, phenyl or phenyl substituted by R18 and/or R19 and/or R20,
R16 and R17 are independent from each other and are hydrogen, 1–7C-alkyl, 3–7C-cycloalkyl, 3–7C-cycloalkylmethyl, phenyl or phenyl substituted by R18 and/or R19 and/or R20, or R16 and R17 together and with inclusion of the nitrogen atom to which they are bonded, form a 4-morpholinyl-, 1-pyrrolidinyl-, 1-piperidinyl-, 1-hexahydroazepino- or a 1-piperazinyl-ring of formula (c)

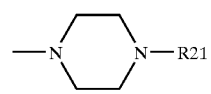

(c)

wherein
R21 is pyrid-4-yl, pyrid-4-ylmethyl, 1–4C-alkyldimethylamino, dimethylaminocarbonylmethyl, N-methyl-piperidin- 4-yl, 4-morpholino-ethyl or tetrahydrofuran-2-ylmethyl,
R18 is halogen, nitro, cyano, carboxyl, 1–4C-alkyl, trifluoromethyl, 1–4C-alkoxy, 1–4C-alkoxycarbonyl, amino, mono- or di-1–4C-alkylamino, aminocarbonyl 1–4C-alkylcarbonylamino or mono- or di-1–4C-alkylaminocarbonyl,
R19 is halogen, amino, nitro, 1–4C-alkyl or 1–4C-alkoxy,
R20 is halogen,
Hetaryl is pyrimidin-2-yl, thieno-[2,3-d]pyrimidin-4-yl, 1-methyl-1H-pyrazolo-[3,4-d]pyrimidin-4-yl, thiazolyl, imidazolyl or furanyl,
Aryl1 is pyridyl, phenyl or phenyl substituted by R18 and/or R19,
Aryl2 is pyridyl, phenyl, phenyl substituted by R18 and/or R19, 2-oxo-2H-chromen-7-yl or 4-(1,2,3-thiadiazol-4-yl)phenyl, n is an integer from 1 to 4,
m is an integer from 1 to 4,
or a hydrate, salt or hydrate of a salt thereof.

2. A compound of formula I according to claim 1, in which
R1 and R2 are both hydrogen or together form an additional bond,
R3 represents a benzene derivative of formula (a) or (b)

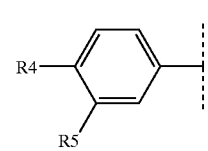

(a)

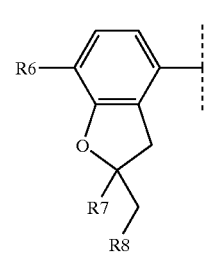

(b)

wherein
R4 is 1–4C-alkoxy or 1–4C-alkoxy which is completely or predominantly substituted by fluorine,
R5 is 1–8C-alkoxy, 3–7C-cycloalkoxy, 3–7C-cycloalkylmethoxy, or 1–4C-alkoxy which is completely or predominantly substituted by fluorine,
R6 is 1–4C-alkoxy, 3–5C-cycloalkoxy, 3–5C-cycloalkylmethoxy, or 1–4C-alkoxy which is completely or predominantly substituted by fluorine,
R7 is 1–4C-alkyl and
R8 is hydrogen or 1–4C-alkyl,
or wherein
R7 and R8 together and with inclusion of the two carbon atoms, to which they are bonded, form a spiro-linked 5-, 6- or 7-membered hydrocarbon ring, optionally interrupted by an oxygen or sulphur atom,
R9 is —S(O)$_2$—R10, —S(O)$_2$—(CH$_2$)$_n$—R11, —(CH$_2$)$_m$—S(O)$_2$—R12, —C(O)R13, —C(O)—(CH$_2$)$_n$—R14, —(CH$_2$)$_m$—C(O)—R15, Hetaryl, Aryl1 or Aryl2-1–4C-alkyl,
R10 is 1–4C-alkyl, 5-dimethylaminonaphthalin-1-yl, —N(R16)R17, phenyl or phenyl substituted by R18 and/or R19,
R11 is —N(R16)R17,
R12 is —N(R16)R17,
R13 is 1–4C-alkyl, hydroxycarbonyl-1–4C-alkyl, phenyl, pyridyl, 4-ethyl-piperazin-2,3-dion-1-yl or —N(R16)R17,
R14 is —N(R16)R17,
R15 is —N(R16)R17, phenyl, phenyl substituted by R18 and/or R19 and/or R20,
R16 and R17 are independent from each other and are hydrogen, 1–7C-alkyl, 3–7C-cycloalkyl, 3–7C-cycloalkylmethyl or phenyl, or R16 and R17 together, and with inclusion of the nitrogen atom to which they are bonded, form a 4-morpholinyl-, 1-pyrrolidinyl-, 1-piperidinyl-, 1-hexahydroazepino- or a 1-piperazinyl-ring of formula (c)

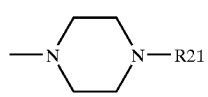

wherein
R21 is pyrid-4-yl, pyrid-4-ylmethyl, 1–4C-alkyl-dimethylamino, dimethylaminocarbonylmethyl, N-methyl-piperidin-4-yl, 4-morpholino-ethyl or tetrahydrofuran-2-ylmethyl, R18 is halogen, nitro, cyano, carboxyl, 1–4C-alkyl, trifluoromethyl, 1–4C-alkoxy, 1–4C-alkoxycarbonyl, amino, mono- or di-1–4C-alkylamino, aminocarbonyl 1–4C-alkylcarbonylamino or mono- or di-1–4C-alkylaminocarbonyl, R19 is halogen, amino, nitro, 1–4C-alkyl or 1–4C-alkoxy, R20 is halogen, Hetaryl is pyrimidin-2-yl, thieno-[2,3-d]pyrimidin-4-yl, 1-methyl-1H-pyrazolo-[3,4-d]pyrimidin-4-yl, thiazolyl, imidazolyl or furanyl, Aryl1 is pyridyl, phenyl or phenyl substituted by R18 and/or R19, Aryl2 is pyridyl, phenyl, phenyl substituted by R18 and/or R19, 2-oxo-2H-chromen-7-yl or 4-(1,2,3-thiadiazol-4-yl)phenyl, n is an integer from 1 to 4, m is an integer from 1 to 4, or a hydrate, salt or hydrate of a salt thereof.

3. A compound of formula I according to claim 1, in which

R1 and R2 are both hydrogen or together form an additional bond,

R3 represents a benzene derivative of formula (a) or (b)

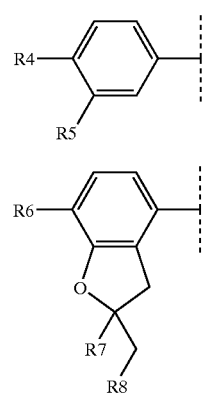

wherein
R4 is 1–4C-alkoxy or 1–2C-alkoxy which is completely or predominantly substituted by fluorine,
R5 is 1–4C-alkoxy,
R6 is 1–2C-alkoxy or 1–2C-alkoxy which is completely or predominantly substituted by fluorine,
R7 is methyl and
R8 is hydrogen,
or wherein
R7 and R8 together and with inclusion of the two carbon atoms, to which they are bonded, form a spiro-linked cyclopentane, cyclohexane, tetrahydrofurane or tetrahydropyran ring, R9 is —S(O)$_2$—R10, —S(O)$_2$—(CH$_2$)$_n$—R11, —C(O)R13, —C(O)—(CH$_2$)$_n$—R14, —(CH$_2$)$_m$—C(O)—R15, Hetaryl, Aryl1 or Aryl2-1–2C-alkyl, R10 is 1–4C-alkyl, 5-dimethylaminonaphthalin-1-yl, —N(R16)R17, phenyl or phenyl substituted by R18, R11 is —N(R16)R17, R13 is 1–4C-alkyl, hydroxycarbonyl-1–4C-alkyl, phenyl, pyridyl, 4-ethyl-piperazin-2,3-dion-1-yl or —N(R16)R17, R14 is —N(R16)R17, R15 is —N(R16)R17, phenyl or phenyl substituted by R18 and/or R19 and/or R20, R16 and R17 are independent from each other and are hydrogen, 1–4C-alkyl, phenyl or phenyl substituted by R18 and/or R19 and/or R20, or R16 and R17 together and with inclusion of the nitrogen atom to which they are bonded, form a 4-morpholinyl ring, a 1-piperidinyl ring or a 1-piperazinyl ring of formula (c)

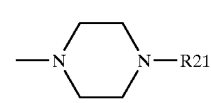

wherein
R21 is pyrid-4-yl, pyrid-4-ylmethyl, dimethylamino-1–4C-alkyl, dimethylaminocarbonylmethyl, N-methyl-piperidin-4-yl, 4-morpholino-ethyl or tetrahydrofuran-2-ylmethyl, R18 is halogen, nitro, 1–4C-alkyl, trifluoromethyl, 1–4C-alkoxy or 1–4C-alkoxycarbonyl, R19 is halogen, amino, nitro, 1–4C-alkyl or 1–4C-alkoxy, R20 is halogen, Hetaryl is pyrimidin-2-yl, thieno-[2,3-d]pyrimidin-4-yl or 1-methyl-1H-pyrazolo-[3,4-d]pyrimidin-4-yl, Aryl1 is pyridyl, phenyl or phenyl substituted by R18, Aryl2 is pyridyl, phenyl, phenyl substituted by R18, 2-oxo-2H-chromen-7-yl or 4-(1,2,3-thiadiazol-4-yl)phenyl, n is 1 or 2, m is 1 or 2, or a hydrate, salt or hydrate of a salt thereof.

4. A compound of formula I according to claim 1, in which

R1 and R2 are both hydrogen or together form an additional bond,

R3 represents a benzene derivative of formula (a) or (b)

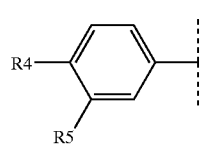

-continued

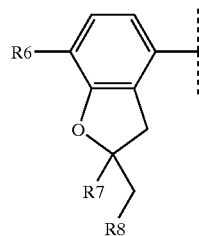
(b)

wherein
R4 is 1–2C-alkoxy or 1–2C-alkoxy which is completely or predominantly substituted by fluorine,
R5 is 1–4C-alkoxy,
R6 is 1–2C-alkoxy or 1–2C-alkoxy which is completely or predominantly substituted by fluorine,
R7 is methyl and
R8 is hydrogen,
or wherein
R7 and R8 together and with inclusion of the two carbon atoms, to which they are bonded, form a spiro-linked cyclopentane, cyclohexane, tetrahydrofurane or tetrahydropyran ring,
R9 is —S(O)$_2$—10, —S(O)$_2$—(CH$_2$)$_n$—R11, —C(O)R13, —C(O)—(CH$_2$)$_n$—R14, —(CH$_2$)$_m$—C(O)—R15, Hetaryl, Aryl1 or Aryl2-1–2C-alkyl,
R10 is 1–4C-alkyl, 5-dimethylaminonaphthalin-1-yl, —N(R16)R17, phenyl or phenyl substituted by R18,
R11 is —N(R16)R17,
R13 is 14C-alkyl, hydroxycarbonyl-1–4C-alkyl, phenyl, pyridyl, 4-ethyl-piperazin-2,3-dion-1-yl or —N(R16)R17,
R14 is —N(R16)R17,
R15 is —N(R16)R17, phenyl or phenyl substituted by R18 and/or R19 and/or R20,
R16 and R17 are independent from each other and are hydrogen, 1–4C-alkyl or phenyl, or —R16 and R17 together and with inclusion of the nitrogen atom to which they are bonded, form a 4-morpholinyl-, a 1-piperidinyl or a 1-piperazinyl-ring of formula (c)

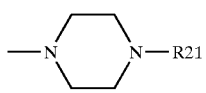
(c)

wherein
R21 is pyrid-4-yl, pyrid-4-ylmethyl, 1–4C-alkyl-dimethylamino, dimethylaminocarbonylmethyl, N-methyl-piperidin-4-yl, 4-morpholino-ethyl or tetrahydrofuran-2-ylmethyl,
R18 is halogen, nitro, 1–4C-alkyl, trifluoromethyl or 1–4C-alkoxy,
R19 is halogen, amino, nitro, 1–4C-alkyl or 1–4C-alkoxy,
R20 is halogen,
Hetaryl is pyrimidin-2-yl, thieno-[2,3-d]pyrimidin-4-yl or 1-methyl-1H-pyrazolo-[3,4-d]pyrimidin-4-yl,
Aryl1 is pyridyl, phenyl or phenyl substituted by R18,
Aryl2 is pyridyl, phenyl, phenyl substituted by R18, 2-oxo-2H-chromen-7-yl or 4-(1,2,3-thiadiazol-4-yl)phenyl, n is 1 or 2,
m is 1 or 2,
or a hydrate, salt or hydrate of a salt thereof.
5. A compound of formula I according to claim 1, in which
R1 and R2 together form an additional bond,
R3 represents a benzene derivative of formula (a) or (b)

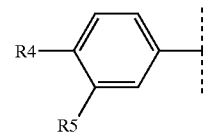
(a)

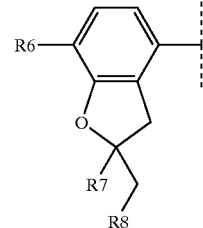
(b)

wherein
R4 is 1–4C-alkoxy,
R5 is 1–4C-alkoxy,
R6 is 1–2C-alkoxy,
R7 is methyl and
R8 is hydrogen,
R9 is —S(O)$_2$—R10, —C(O)R13, —C(O)—(CH$_2$)$_n$—R14, —(CH$_2$)$_m$—C(O)—R15, Hetaryl, Aryl1 or Aryl2-1–2C-alkyl,
R10 is 1–4C-alkyl, 5-dimethylaminonaphthalin-1-yl, phenyl or phenyl substituted by R18,
R13 is 1–4C-alkyl, hydroxycarbonyl-1–4C-alkyl, pyridyl, 4-ethyl-piperazin-2,3-dion-1-yl or —N(R16)R17,
R14 is —N(R16)R17,
R15 is —N(R16)R17, phenyl or phenyl substituted by R18 and/or R19 and/or R20,
R16 and R17 are independent from each other and are hydrogen, 1–4C-alkyl, phenyl or phenyl substituted by R18 and/or R19 and/or R20, or R16 and R17 together and with inclusion of the nitrogen atom to which they are bonded, form a 4-morpholinyl ring or a 1-piperazinyl ring of formula (c)

(c)

wherein
R21 is dimethylamino-1–4C-alkyl,
R18 is halogen, nitro, 1–4C-alkyl or 1–4C-alkoxycarbonyl,
R19 is amino,
R20 is halogen,
Hetaryl is pyrimidin-2-yl, thieno-[2,3-d]pyrimidin-4-yl or 1-methyl-1H-pyrazolo-[3,4-d]pyrimidin-4-yl,
Aryl1 is phenyl or phenyl substituted by R18,
Aryl2 is pyridyl, phenyl, 2-oxo-2H-chromen-7-yl or 4-(1,2,3-thiadiazol-4-yl)phenyl, n is 1 or 2,
m is 1 or 2,
or a hydrate, salt or hydrate of a salt thereof.

6. A compound of formula I

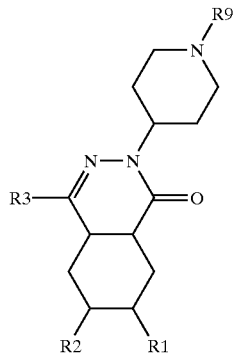

(I)

in which
R1 and R2 together form an additional bond,
R3 represents a benzene derivative of formula (a) or (b)

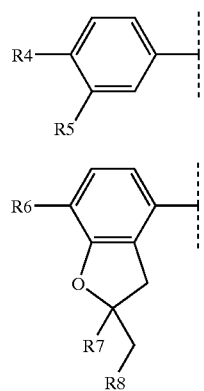

wherein
R4 is methoxy or ethoxy,
R5 is methoxy or ethoxy,
R6 is methoxy or ethoxy,
R7 is methyl and
R8 is hydrogen,
R9 is toluene-4-sulfonyl, methanesulfonyl, acetyl, 5oxo-pentanoic acid, pyridin-4-yl-carbonyl, tert-butylaminocarbonyl, phenylaminocarbonyl, 5-dimethylamino-naphthalene-1-sulfonyl, 4-nitrophenyl, pyridin-4-ylmethyl, morpholine-4-carbonyl, 2-(4-amino-3,5-dichlorophenyl)-2-oxo-ethyl, 1-methyl-1H-pyrazolo[3,4-d]pyrimidin-4-yl, thieno[2,3-d]pyrimidin-4-yl, pyrimidin-2-yl, 2-oxo-2H-chromen-7-ylmethyl, isopropyl, morpholin-4-yl-2-oxo-ethyl, phenethyl, pyridin-3-ylmethyl, pyridin-2-ylmethyl, pyridin-4-ylmethyl, 2-morpholin-4-ylethanoyl, 2-[(4-(2-dimethylaminoethyl)-piperazin-1-yl]-ethanoyl, isopropylaminocarbonylmethyl, 4ethyl-piperazine-2,3-dione-1-carbonyl, 4-(1,2,3-thiadiazol-4-yl-)benzyl, 4-ethoxycarbonylphenylamino-2-oxo-ethyl or aminocarbonylmethyl,
or a hydrate, salt or hydrate of a salt thereof.

7. A compound of formula I

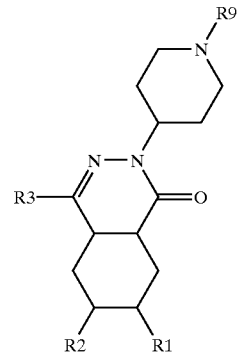

(I)

in which
R1 and R2 together form an additional bond,
R3 represents a benzene derivative of formula (a) or (b)

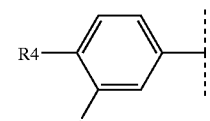

(a)

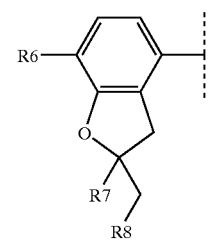

(b)

wherein
R4 is methoxy or ethoxy,
R5 is methoxy or ethoxy,
R6 is methoxy or ethoxy,
R7 is methyl and
R8 is hydrogen,
or wherein
R7 and R8 together and with inclusion of the two carbon atoms, to which they are bonded, form a cyclopentane or cyclohexan ring,
R9 is toluene-4-sulfonyl, methanesulfonyl, acetyl, 5oxo-pentanoic acid, pyridin-4-yl-carbonyl, tert-butylaminocarbonyl, phenylaminocarbonyl, 5-dimethylamino-naphthalene-1-sulfonyl, 4-nitrophenyl, pyridin-4-ylmethyl, morpholine-4-carbonyl, 2-(4-amino-3,5-dichlorophenyl)-2-oxo-ethyl, 1-methyl-1H-pyrazolo[3,4-d]pyrimidin-4-yl, thieno[2,3-d]pyrimidin-4-yl, pyrimidin-2-yl, 2-oxo-2H-chromen-7-ylmethyl, isopropyl, morpholin-4-yl-2-oxo-ethyl, phenethyl, pyridin-3-ylmethyl, pyridin-2-ylmethyl, pyridin-4-ylmethyl, 2-morpholin-4-ylethanoyl, 2-[4-(2-dimethylaminoethyl)-piperazin-1-yl]-ethanoyl, isopropylaminocarbonylmethyl, 4-ethyl-piperazine-2,3-dione-1-carbonyl or 4-(1,2,3-thiadiazol-4-yl-)benzyl,
or a hydrate, salt or hydrate of a salt thereof.

8. A compound of formula I according to claim 1 or a hydrate, salt or hydrate of a salt thereof, in which the hydrogen atoms in the positions 4a and 8a are cis-configurated.

9. A compound of formula I according to claim 1 or a hydrate, salt or hydrate of a salt thereof, in which the absolute configuration is S in the position 4a and R in the position 8a.

10. A compound of formula I according to claim 1 or a hydrate, salt or hydrate of a salt thereof, in which R3 represents a benzene derivative of formula (a).

11. A compound of formula I according to claim 1, selected from the group consisting of (4aS,8aR)-4-(3,4-Diethoxyphenyl)2-[1-(toluene-4-sulfonyl)-piperidin-4-yl]-4a,5,8,8a-tetrahydro-2H-phthalazin-1-one, (4aS,8aR)-4-(3,4-Diethoxyphenyl)-2-(1-methanesulfonyl-piperidin-4-yl)-4a,5,8,8a-tetrahydro-2H-phthalazin-1-one, (4aS,8aR)-2-(1-Acetyl-piperidin-4-yl)-4-(3,4-diethoxyphenyl)-4a,5,8,8a-tetrahydro-2H-phthalazin-1-one, 5-(4-[(4aS,8aR)-4-(3,4-Diethoxy-phenyl)-1-oxo-4a,5,8,8a-tetrahydro-1H-phthalazin-2-yl]-piperidin-1-yl)-5-oxo-pentanoic acid, (4aS,8aR)-4-(3,4-Diethoxyphenyl)-2-[1-(1-pyridin-4-yl-methanoyl)-piperidin-4-yl]-4a,5,8,8a-tetrahydro-2H-phthalazin-1-one, 4-[(4aS,8aR)-4-(3,4-Diethoxyphenyl)-1-oxo-4a,5,8,8a-tetrahydro-1H-phthalazin-2-yl]-piperidine-1-carboxylic acid tert-butylamide, 4-[(4aS,8aR)-4-(3,4-Diethoxyphenyl)-1-oxo-4a,5,8,8a-tetrahydro-1H-phthalazin-2-yl]-piperidine-1-carboxylic acid phenylamide, 4-[(4aS,8aR)-4-(3,4-Dimethoxyphenyl)-1-oxo-4a,5,8,8a-tetrahydro-1H-phthalazin-2-yl]-piperidine-1-carboxylic acid tert-butylamide, (cis)-4-[4-(7-Methoxy-2,2-dimethyl-2,3-dihydro-benzofuran-4-yl)-1-oxo-4a,5,8,8a-tetrahydro-1H-phthalazin-2-yl]-piperidine-1-carboxylic acid tert-butylamide, (4aS,8aR)-4-(3,4-Dimethoxyphenyl)-2-[1-(5-dimethylamino-naphthalene-1-sulfonyl)-piperidin-4-yl]-4a,5,8,8a-tetrahydro-2H-phthalazin-1-one, (4aS,8aR)-4-(3,4-Dimethoxyphenyl)-2-[1-(4-nitrophenyl)-piperidin-4-yl]4a,5,8,8a-tetrahydro-2H-phthalazin-1-one, (4aS,8aR)-4-(3,4-Dimethoxyphenyl)-2-(1-pyridin-4-ylmethyl-piperidin-4-yl)-4a,5,8,8a-tetrahydro-2H-phthalazin-1-one, (4aS,8aR)-4-(3,4-Dimethoxyphenyl)-2-[1-(morpholine-4-carbonyl)-piperidin-4-yl]-4a,5,8,8a-tetrahydro-2H-phthalazin-1-one, (4aS,8aR)-2-{1-[2-(4-Amino-3,5dichloro-phenyl)-2-oxoethyl]-piperidin-4-yl}-4-(3,4-dimethoxy-phenyl)-4a,5,8,8a-tetrahydro-2H-phthalazin-1-one, 4-(3,4-Dimethoxyphenyl)-2-[1-(1-methyl-1H-pyrazolo[3,4-d]pyrimidin-4-yl)-piperidin-4-yl]-4a,5,8,8a-tetrahydro-2H-naphthalen-1-one, (4aS,8aR)-4-(3,4-Dimethoxyphenyl)-2-(1-thieno[2,3-d]pyrimidin-4-yl-piperidin-4-yl)-4a,5,8,8a-tetrahydro-2H-phthalazin-1-one, (4aS,8aR)-4-(3,4-Dimethoxyphenyl)-2-(1-pyrimidin-2-yl-piperidin-4-yl)-4a,5,8,8a-tetrahydro-2H-phthalazin-1-one, (4aS,8aR)-4-(3,4-Dimethoxyphenyl)-2-[1-(2-oxo-2H-chromen-7-ylmethyl)-piperidin-4-yl]-4a,5,8,8a-tetrahydro-2H-phthalazin-1-one, (4aS,8aR)-4-(3,4-Dimethoxyphenyl)-2-[1-(2-morpholin-4-yl-2-oxo-ethyl)-piperidin-4-yl]-4a,5,8,8a-tetrahydro-2H-phthalazin-1-one, (4aS,8aR)-4-(3,4-Dimethoxyphenyl)-2-(1-phenethyl-piperidin-4-yl)-4a,5,8,8tetrahydro-2H-phthalazin-1-one, (4aS,8aR)4-(3,4-Diethoxyphenyl)-2-[1-(morpholine-4-carbonyl)-piperidin-4-yl]-4a,5,8,8a-tetrahydro-2H-phthalazin-1-one, (4aS,8aR)-4-(3,4-Dimethoxyphenyl)-2-(1-pyridin-3-ylmethyl-piperidin-4-yl)-4a,5,8,8a-tetrahydro-2H-phthalazin-1 one, (4aS,8aR)-4-(3,4-Dimethoxy-phenyl)-2-(1-pyridin-2-ylmethyl-piperidin-4-yl)-4a,5,8,8a-tetrahydro-2H-phthalazin-1-one, (4aS,8aR)-4-(3,4-Diethoxyphenyl)-2-[1-(2-morpholin-4-yl-ethanoyl)-piperidin-4-yl]-4a,5,8,8a-tetrahydro-2H-phthalazin-1-one, (4aS,8aR)-4-(3,4-Diethoxyphenyl)-2-(1-{2-[4-(2-dimethylamino-ethyl-piperazin-1-yl]-ethanoyl}-piperidin-4-yl)-4a,5,8,8a-tetrahydro-2H-phthalazin-1-one, 2-{4-[(4aS,8aR)-4-(3,4-Dimethoxyphenyl)-1-oxo-4a,5,8,8a-tetrahydro-1H-phthalazin-2-yl]-piperidin-1-yl}-2H-isopropyl-acetamide, (4aS,8aR)-4-(3,4-Dimethoxyphenyl)-2-[1-(4–1,2,3-thiadiazol-4-yl-benzyl)-piperidin-4-yl]-4a,5,8,8a-tetrahydro-2H-phthalazin-1-one, 1-(1 {4-[(4aS,8aR)-4-(3,4-Dimethoxyphenyl)-1-oxo-4a,5,8,8a-tetrahydro-1H-phthalazin-2-yl]-piperidin-1-yl}-methanoyl)-4-ethyl-piperazine-2,3-dione, 4-(2{4-[(4aS,8aR)-4-(3,4-Dimethoxy-phenyl)-1-oxo-4a,5,8,8a-tetrahydro-1H-phthalazin-2-yl]-piperidin-1-yl}-ethanoylamino)-benzoic acid ethyl ester, 2-{4-[(4aS,8aR)-4-(3,4-Dimethoxyphenyl)-1-oxo-4a,5,8,8a-tetrahydro-1H-phthalazin-2-yl]-piperidin-1-yl}-acetamide, and the hydrates, salts and hydrates of the salts thereof.

12. A compound of formula I according to claim 2 or a hydrate, salter hydrate of a salt thereof, in which the hydrogen atoms in the positions 4a and 8a are cis-configurated.

13. A compound of formula I according to claim 2 or a hydrate, salt or hydrate of a salt thereof, in which the absolute configuration is S in the position 4a and R in the position 8a.

14. A compound of formula I according to claim 2 or a hydrate, salt or hydrate of a salt thereof, in which R3 represents a benzene derivative of formula (a).

15. A compound of formula I according to claim 3 or a hydrate, salt or hydrate of a salt thereof, in which the hydrogen atoms in the positions 4a and 8a are cis-configurated.

16. A compound of formula I according to claim 3 or a hydrate, salt or hydrate of a salt thereof, In which the absolute configuration is S in the position 4a and P in the position 8a.

17. A compound of formula I according to claim 3 or a hydrate, salt or hydrate of a salt thereof, in which R3 represents a benzene derivative of formula (a).

18. A compound of formula I according to claim 4 or a hydrate, salt or hydrate of a salt thereof, in which the hydrogen atoms in the positions 4a and 8a are cis-configurated.

19. A compound of formula I according to claim 4 or a hydrate, salt or hydrate of a salt thereof, in which the absolute configuration is S in the position 4a and R in the position 8a.

20. A compound of formula I according to claim 4 or a hydrate, salt or hydrate of a salt thereof, in which R3 represents a benzene derivative of formula (a).

21. A compound of formula I according to claim 5 or a hydrate, salt or hydrate of a salt thereof, in which the hydrogen atoms in the positions 4a and 8a are cis-configurated.

22. A compound of formula I according to claim 5 or a hydrate, salt or hydrate of a salt thereof, in which the absolute configuration is S in the position 4a and R in the position 8a.

23. A compound of formula I according to claim 5 or a hydrate, salt or hydrate of a salt thereof, in which R3 represents a benzene derivative of formula (a).

24. A compound of formula I according to claim 6 or a hydrate, salt or hydrate of a salt thereof, in which the hydrogen atoms in the positions 4a and 8a are cis-configurated.

25. A compound of formula I according to claim 6 or a hydrate, salt or hydrate of a salt thereof, in which the absolute configuration is S in the position 4a and R in the position 8a.

26. A compound of formula I according to claim 6 or a hydrate, salt or hydrate of a salt thereof, in which R3 represents a benzene derivative of formula (a).

27. A compound of formula I according to claim 7 or a hydrate, salt or hydrate of a salt thereof, in which the hydrogen atoms in the positions 4a and 8a are cis-configurated.

28. A compound of formula I according to claim 7 or a hydrate, salt or hydrate of a salt thereof, in which the absolute configuration is S in the position 4a and R in the position 8a.

29. A compound of formula I according to claim 7 or a hydrate, salt or hydrate or a salt thereof, in which R3 represents a benzene derivative of formula (a).

* * * * *

UNITED STATES PATENT AND TRADEMARK OFFICE
CERTIFICATE OF CORRECTION

PATENT NO. : 6,953,853 B2
DATED : October 11, 2005
INVENTOR(S) : Grundler et al.

It is certified that error appears in the above-identified patent and that said Letters Patent is hereby corrected as shown below:

Column 21,
Line 14, delete "carbon atoms, to" and replace with -- carbon atoms to --.
Line 16, delete "sulphur" and replace with -- sulfur --.
Line 51, delete "N-methyl-piperidin- 4-yl," and replace with -- N-methyl-piperidin-4-yl, --.

Column 22,
Line 40, delete "together and" and replace with -- together, and --.
Line 41, delete "carbon atoms, to" and replace with -- carbon atoms to --.
Line 44, delete "sulphur" and replace with -- sulfur --.
Line 59, delete "phenyl, phenyl substituted" and replace with -- phenyl or phenyl substituted --.

Column 23,
Lines 15-16, delete "aminocarbonyl 1-4C-alkylcarbonylamino" and replace with -- aminocarbonyl, 1-4C-alkylcarbonylamino --.
Line 64, delete "together and" and replace with -- together, and --.
Line 65, delete "carbon atoms, to" and replace with -- carbon atoms to --.

Column 24,
Lines 18-19, delete "together and" and replace with -- together, and --.

Column 25,
Line 24, delete "carbon atoms, to" and replace with -- carbon atoms to --.
Line 27, delete "-S(O)$_2$-10," and replace with -- -S(O)$_2$-R10, --.
Line 34, delete "14C-alkyl," and replace with -- 1-4C-alkyl, --.
Line 41, delete "-R16" and replace with -- R16 --.

Column 27,
Lines 51-52, delete "5oxo-pentanoic" and replace with -- 5-oxo-pentanoic --.
Lines 63-64, delete "4ethyl-piperazine-2,3-dione-l-carbonyl," and replace with -- 4-ethyl-piperazine-2,3-dione-l-carbonyl, --.
Lines 64-65, delete "4-(1,2,3-thiadiazol-4-yl-)benzyl" and replace with -- 4-(1,2,3-thiadiazol-4-yl)benzyl --.

Column 28,
Line 47, delete "carbon atoms, to" and replace with -- carbon atoms to --.
Lines 49-50, delete "5oxo-pentanoic" and replace with -- 5-oxo-pentanoic --.

UNITED STATES PATENT AND TRADEMARK OFFICE
CERTIFICATE OF CORRECTION

PATENT NO.     : 6,953,853 B2
DATED          : October 11, 2005
INVENTOR(S)    : Grundler et al.

It is certified that error appears in the above-identified patent and that said Letters Patent is hereby corrected as shown below:

Column 29,
Lines 19-21, delete "5-4-[(4aS,8aR)-4-(3,4-Diethoxy-phenyl)-1-oxo-4a,5,8,8a-tetrahydro-1H-phthalazin-2-yl]-piperidin-1-yl)-5-oxo-pentanoic acid" and replace with -- 5-{4-[(4aS,8aR)-4-(3,4-Diethoxy-phenyl)-1-oxo-4a,5,8,8a-tetrahydro-1H-phthalazin-2-yl]-piperidin-l-yl}-5-oxo-pentanoic acid --.
Lines 52-55, delete "(4aS,8aR)-2-{l-[2-(4-Amino-3,5dichloro-phenyl)-2-oxo-ethyl]-piperidin-4-yl}-4-(3,4-dimethoxy-phenyl)-4a,5,8,8a-tetrahydro-2H-phthalazin-l-one," and replace with -- (4aS,8aR)-2-{1-[2-(4-Amino-3,5-dichloro-phenyl)-2-oxo-ethyl]-piperidin-4-yl}-4-(3,4-dimethoxy-phenyl)-4a,5,8,8a-tetrahydro-2H-phthalazin-1-one, --.

Column 30,
Lines 4-6, delete "(4aS,8aR)-4-(3,4-Dimethoxyphenyl)-2-(1-phenethyl-piperidin-4-yl)-4a,5,8,8tetrahydro-2H-phthalazin-l-one" and replace with -- (4aS,8aR)-4-(3,4-Dimethoxyphenyl)-2-(1-phenethyl-piperidin-4-yl)-4a,5,8,8a-tetrahydro-2H-phthalazin-l-one --.
Lines 7-9, delete "(4aS,8aR)4-(3,4-Diethoxyphenyl)-2-[1-(morpholine-4-carbonyl)-piperidin-4-yl)-4a,5,8,8a-tetrahydro-2H-phthalazin-l-one," and replace with -- (4aS,8aR)-4-(3,4-Diethoxyphenyl)-2-[1-(morpholine-4-carbonyl)-piperidin-4-yl)-4a,5,8,8a-tetrahydro-2H-phthalazin-l-one, --.
Lines 19-22, delete "(4aS,8aR)-4-(3,4-Diethoxyphenyl)-2-(1-{2-[4-(2-dimethylamino-ethyl-piperazin-l-yl]-ethanoyl}-piperidin-4-yl)-4a,5,8,8a-tetrahydro-2H-phthalazin-1-one," and replace with -- (4aS,8aR)-4-(3,4-Diethoxyphenyl)-2-(1-{2-[4-(2-dimethylamino-ethyl)piperazin-l-yl]-ethanoyl}-piperidin-4-yl)-4a,5,8,8a-tetrahydro-2H-phthalazin-1-one, --.
Lines 23-25, delete "2-{4-[(4aS,8aR)-4-(3,4-Dimethoxyphenyl)-l-oxo-4a,5,8,8a-tetrahydro-1H-phthalazin-2-yl]-piperidin-l-yl}-2H-isopropyl-acetamide" and replace with -- 2-{4-[(4aS,8aR)-4-(3,4-Dimethoxyphenyl)-l-oxo-4a,5,8,8a-tetrahydro-1H-phthalazin-2-yl]-piperidin-1-yl}-N-isopropyl-acetamide --.
Lines 29-31, delete "1-(l {4-[(4aS,8aR)-4-(3,4-Dimethoxyphenyl)-1-oxo-4a,5,8,8a-tetrahydro-1H-phthalazin-2-yl]-piperidin-l-yl}-methanoyl)-4-ethyl-piperazine-2,3-dione," and replace with -- 1-(1-{4-[(4aS,8aR)-4-(3,4-Dimethoxyphenyl)-1-oxo-4a,5,8,8a-tetrahydro-1H-phthalazin-2-yl]-piperidin-l-yl}-methanoyl)-4-ethyl-piperazine-2,3-dione, --.
Lines 32-34, delete "4-(2{4-[(4aS,8aR)-4-(3,4-Dimethoxy-phenyl)-l-oxo-4a,5,8,8a-tetrahydro-1H-phthalazin-2-yl]-piperidin-l-yl}-ethanoylamino)-benzoic acid ethyl ester" and replace with -- 4-(2-{4-[(4aS,8aR)-4-(3,4-Dimethoxy-phenyl)-1-oxo-4a,5,8,8a-tetrahydro-1H-phthalazin-2-yl]-piperidin-l-yl}-ethanoylamino)-benzoic acid ethyl ester --.
Line 40, delete "salter hydrate" and replace with -- salt or hydrate --.

UNITED STATES PATENT AND TRADEMARK OFFICE
CERTIFICATE OF CORRECTION

PATENT NO. : 6,953,853 B2
DATED : October 11, 2005
INVENTOR(S) : Grundler et al.

It is certified that error appears in the above-identified patent and that said Letters Patent is hereby corrected as shown below:

<u>Column 30 (cont'd),</u>
Line 54, delete "thereof, In which" and replace with -- thereof, in which --.
Line 55, delete "position 4a and P in" and replace with -- position 4a and R in --.

Signed and Sealed this

Twenty-eighth Day of February, 2006

JON W. DUDAS
*Director of the United States Patent and Trademark Office*